United States Patent
Duve (10) Patent No.: US 8,663,481 B2
(45) Date of Patent: Mar. 4, 2014

(54) METHOD OF TREATING WATER WITH CHLORINE DIOXIDE

(75) Inventor: Hans Duve, Duelmen (DE)

(73) Assignee: Infracor GmbH, Marl (DE)

( * ) Notice: Subject to any disclaimer, the term of this patent is extended or adjusted under 35 U.S.C. 154(b) by 0 days.

(21) Appl. No.: 13/109,508

(22) Filed: May 17, 2011

(65) Prior Publication Data
US 2011/0220587 A1    Sep. 15, 2011

Related U.S. Application Data

(63) Continuation of application No. 12/339,533, filed on Dec. 19, 2008, now abandoned.

(30) Foreign Application Priority Data

Dec. 19, 2007  (DE) .......................... 10 2007 061 360
Aug. 7, 2008   (DE) .......................... 10 2008 041 081
Sep. 29, 2008  (DE) .......................... 10 2008 042 424

(51) Int. Cl.
*C02F 1/76* (2006.01)

(52) U.S. Cl.
USPC ........... 210/754; 210/765; 210/192; 423/477; 252/187.21

(58) Field of Classification Search
USPC .............................. 210/753–756, 764, 167.3, 210/170.01–170.11, 192, 198.1, 205, 209, 210/220; 423/477; 366/167.1; 252/187.21
See application file for complete search history.

(56) References Cited

U.S. PATENT DOCUMENTS

| | | |
|---|---|---|
| 1,937,780 A | 12/1933 | Ornstein |
| 4,013,761 A | 3/1977 | Ward et al. |
| 4,019,983 A | 4/1977 | Mandt |
| 4,104,190 A | 8/1978 | Hartshorn |
| 4,210,534 A | 7/1980 | Molvar |
| 4,247,531 A | 1/1981 | Hicks |
| 4,250,144 A | 2/1981 | Ratigan |
| 4,251,224 A | 2/1981 | Gowley et al. |
| 4,287,054 A | 9/1981 | Hollingsworth |
| 4,414,193 A | 11/1983 | Fredette et al. |
| 4,534,952 A | 8/1985 | Rapson et al. |
| 4,618,479 A | 10/1986 | Santillie et al. |

(Continued)

FOREIGN PATENT DOCUMENTS

| | | |
|---|---|---|
| DE | 1 069 122 | 8/1958 |
| DE | 1 203 691 | 10/1965 |

(Continued)

OTHER PUBLICATIONS

Definition of "appliance" from yourdictionary.com (obtained Nov. 2010).*

(Continued)

*Primary Examiner* — Lucas Stelling
(74) *Attorney, Agent, or Firm* — Oblon, Spivak, McClelland, Maier & Neustadt, L.L.P.

(57) ABSTRACT

A method of treating water with chlorine dioxide ($ClO_2$), by: surrounding a reaction chamber, in which the $ClO_2$ is generated, with water, wherein the water surrounding the reaction chamber is simultaneously the water to be treated; and passing a reaction solution comprising the $ClO_2$ formed in the reaction chamber out of the reaction chamber through an outlet directly into the water, thus treating the water.

26 Claims, 3 Drawing Sheets

(56) References Cited

U.S. PATENT DOCUMENTS

| | | |
|---|---|---|
| 4,820,408 A | 4/1989 | Sandig |
| 5,120,452 A | 6/1992 | Ness et al. |
| 5,204,081 A | 4/1993 | Mason et al. |
| 5,227,306 A | 7/1993 | Eltomi et al. |
| 5,290,524 A | 3/1994 | Rosemblatt et al. |
| 5,318,702 A | 6/1994 | Ashbrook |
| 5,324,497 A | 6/1994 | Westerlund |
| 5,382,520 A | 1/1995 | Jenson et al. |
| 5,435,913 A | 7/1995 | Ashbrook |
| 5,458,858 A | 10/1995 | Dawkins |
| 5,565,182 A | 10/1996 | Sokol |
| 5,611,920 A * | 3/1997 | Simpson et al. ............ 210/192 |
| 5,651,996 A | 7/1997 | Roozdar |
| 5,993,669 A | 11/1999 | Fulmer |
| 6,051,135 A | 4/2000 | Lee et al. |
| 6,083,457 A | 7/2000 | Parkinson et al. |
| 6,325,970 B1 | 12/2001 | Parkinson et al. |
| 6,436,345 B1 | 8/2002 | Roensch et al. |
| 6,468,479 B1 | 10/2002 | Mason et al. |
| 6,497,822 B2 | 12/2002 | Blanchette et al. |
| 6,576,144 B1 * | 6/2003 | Vineyard ................ 210/758 |
| 6,645,457 B2 | 11/2003 | Mason et al. |
| 6,716,354 B2 | 4/2004 | Rosenblatt et al. |
| 6,761,872 B2 | 7/2004 | Roensch et al. |
| 6,767,470 B2 | 7/2004 | Iverson et al. |
| 6,790,427 B2 | 9/2004 | Charles et al. |
| 6,982,040 B2 | 1/2006 | Costa et al. |
| 7,011,751 B1 | 3/2006 | Waldner et al. |
| 7,077,995 B2 | 7/2006 | Roensch et al. |
| 7,094,353 B2 | 8/2006 | Unhoch |
| 7,128,879 B1 | 10/2006 | Hunt et al. |
| 7,147,786 B2 | 12/2006 | Costa et al. |
| 7,186,376 B2 | 3/2007 | Iverson et al. |
| 7,220,367 B2 | 5/2007 | Speronello et al. |
| 7,255,797 B2 | 8/2007 | Martin |
| 7,261,821 B2 | 8/2007 | Beardwood |
| 7,285,255 B2 | 10/2007 | Kadlec et al. |
| 7,320,761 B2 | 1/2008 | Costa et al. |
| 7,326,352 B2 | 2/2008 | Waldner et al. |
| 7,449,119 B2 | 11/2008 | Brown |
| 7,452,511 B2 | 11/2008 | Schmitz et al. |
| 7,571,676 B2 | 8/2009 | Nelson |
| 7,575,673 B2 | 8/2009 | Unhoch |
| 7,713,501 B2 | 5/2010 | Priegel |
| 7,744,765 B2 | 6/2010 | Bjerkan et al. |
| 7,754,082 B2 | 7/2010 | Speece et al. |
| 2003/0138371 A1 | 7/2003 | McWhorter et al. |
| 2004/0101438 A1 | 5/2004 | Nelson et al. |
| 2004/0175322 A1 | 9/2004 | Woodruff et al. |
| 2004/0222166 A1 * | 11/2004 | Van Vossen et al. ......... 210/764 |
| 2004/0256330 A1 | 12/2004 | Okasaki |
| 2005/0155936 A1 | 7/2005 | Martin et al. |
| 2005/0244328 A1 * | 11/2005 | Schmitz et al. ............ 423/477 |
| 2006/0016765 A1 | 1/2006 | DiPietro et al. |
| 2006/0120945 A1 | 6/2006 | Warner et al. |
| 2007/0034570 A1 | 2/2007 | DiMascio |
| 2007/0272622 A1 | 11/2007 | Mercer et al. |
| 2008/0006586 A1 | 1/2008 | Axtell et al. |
| 2008/0217258 A1 | 9/2008 | Buchan |
| 2009/0159538 A1 | 6/2009 | Duve |
| 2009/0173697 A1 | 7/2009 | Axtell et al. |
| 2009/0246074 A1 | 10/2009 | Nelson et al. |
| 2010/0006513 A1 | 1/2010 | Fisher et al. |
| 2010/0044320 A1 | 2/2010 | Weber et al. |
| 2010/0074813 A1 | 3/2010 | Dee |
| 2010/0086623 A1 | 4/2010 | Donnan et al. |
| 2010/0155341 A1 | 6/2010 | Duve |

FOREIGN PATENT DOCUMENTS

| | | |
|---|---|---|
| DE | 23 43 171 | 3/1975 |
| DE | 102 25 626 | 12/2003 |
| DE | 20 2004 005 755 | 8/2004 |
| DE | 103 08 046 | 9/2004 |
| DE | 103 26 628 | 1/2005 |
| DE | 20 2005 017 232 | 2/2006 |
| DE | 20 2007 011 108 U1 | 1/2008 |
| DE | 10 2010 025 928 | 1/2012 |
| EP | 0 153 841 A2 | 9/1985 |
| EP | 0 766 996 | 4/1997 |
| EP | 0 866 031 | 9/1998 |
| EP | 1 504 767 | 2/2005 |
| EP | 2 119 686 | 11/2009 |
| IT | 1351156 | 1/2009 |
| JP | 11-10164 | 1/1999 |
| JP | 2002-220207 | 8/2002 |
| JP | 2003-170029 | 6/2003 |
| JP | 2003-260468 | 9/2003 |
| JP | 2004-143004 | 5/2004 |
| JP | 2005-319381 | 11/2005 |
| JP | 2008-094662 | 4/2008 |
| NL | 9300747 | 12/1993 |
| RU | 45378 U2 | 4/2000 |
| RU | 2163882 C2 | 4/2000 |
| WO | WO 01/54786 | 8/2001 |
| WO | WO 2004/078648 | 9/2004 |
| WO | WO 2007/029183 | 3/2007 |
| WO | WO 2008/116724 | 10/2008 |
| WO | WO 2009/077160 | 6/2009 |
| WO | WO 2009/077213 | 6/2009 |
| WO | WO 2009/077309 | 11/2009 |
| WO | WO 2010/069632 | 6/2010 |

OTHER PUBLICATIONS

U.S. Appl. No. 12/734,877, filed Jun. 1, 2010, Belluati, et al.
"Aquacon WHO1 Chlordioxiderzeugung", (Chlordioxid-Erzeugung Nach dem Salzsaure-Chlorit-Verfahren), XP-002507001, Aug. 2008, pp. 1-4.
U.S. Appl. No. 13/641,576, filed Oct. 16, 2012, Duve.
"Disinfectants", Scientific and Research Institute for Technical and Economic Research in Chemical Industry, Survey Information, ISSN 0203-7971, 1986, 3 pages (English Translation).
Office Action issued Aug. 26, 2013, in Japanese Patent Application No. 2010-538540, filed Nov. 28, 2008 (with German-language version).

\* cited by examiner

METHOD OF TREATING WATER WITH CHLORINE DIOXIDE

This application is a Continuation of U.S. application Ser. No. 12/339,533, filed on Dec. 19, 2008, abandoned, and incorporated herein by reference.

BACKGROUND OF THE INVENTION

1. Field of the Invention

The invention relates to a method of treating water with chlorine dioxide ($ClO_2$).

2. Description of the Related Art

Chlorine dioxide is used in water treatment because of its high bactericidal, virucidal and algicidal activity. Due to the explosive tendency of gaseous chlorine dioxide ($c > 300$ g/m$^3$) and chlorine dioxide solutions ($c > 26$ g/l), chlorine dioxide cannot be stored in compressed form or in solutions of relatively high concentration. Owing to these chemical properties, chlorine dioxide must be produced at the point of use. This is conventionally achieved by mixing basic chemicals in special reactors of chlorine dioxide generation systems. The chemical storage vessels, the metering appliances and also the reactor of the chlorine dioxide systems form a locally linked unit of apparatus which is generally erected in rooms accessed by people.

There are a plurality of methods for synthesizing $ClO_2$ which are used commercially for water treatment, but principally three underlying methods are used. These methods use sodium chlorite ($NaClO_2$) as one of the starting materials. The underlying chemistry of the three methods is explained below. The substances used in these methods are termed starting chemicals, or else reactants.

1. Method Using Sodium Chlorite and Strong Acid

In the first method, a strong acid is used together with sodium chlorite. The strong acid is usually hydrochloric acid or sulphuric acid. When hydrochloric acid is used the reaction stoichiometry is as follows:

$$5NaClO_2 + 4HCl \rightarrow 4ClO_2 + 5NaCl + 2H_2O$$

In addition, chlorine dioxide can be formed with the use of sulphuric acid in accordance with the following reaction:

$$10NaClO_2 + 5H_2SO_4 \rightarrow 8ClO_2 + 5Na_2SO_4 + 2HCl + 4H_2O$$

2. Method Starting from Sodium Chlorite and Chlorine

This method uses gaseous chlorine together with sodium chlorite. The reaction proceeds in two stages, first with the formation of hydrochloric acid.

$$Cl_2 + H_2O \rightarrow HOCl + HCl$$

The intermediate, hypochloric acid (HOCl), then reacts with sodium chlorite, forming chlorine dioxide ($ClO_2$).

$$HOCl + HCl + 2NaClO_2 \rightarrow 2ClO_2 + 2NaCl + H_2O$$

The stoichiometric reaction from the two equations is $$Cl_2 + 2NaClO_2 \rightarrow 2ClO_2 + 2NaCl$$

3. Method Starting from Sodium Chlorite and Sodium Hypochlorite

In the third method, sodium hypochlorite (NaOCl) is used together with sodium chlorite:

$$NaOCl + HCl \rightarrow NaCl + HOCl$$

$$HCl + HOCl + 2NaClO_2 \rightarrow 2ClO_2 + 2NaCl + H_2O$$

The synthesis reactions for generating chlorine dioxide are generally carried out in reactors which are operated either continuously or by the batch method.

Two explosion limits must be taken into account in the generation of chlorine dioxide:

more than 6 g of $ClO_2$/l of solution [contact with air] and more than 26 g of $ClO_2$/l of solution [autodecomposition of the aqueous solution]. In the case of the chlorine dioxide syntheses carried out by methods 1 to 3, when use is made of feed chemicals which are passed into the reaction chamber at a concentration of greater than approximately 26 g of $ClO_2$/l of solution, dilution water is added to the reaction chamber in order to bring this concentration below that of spontaneous autodecomposition. The chlorine dioxide solution leaving the reaction chamber which generally contains 20 g of $ClO_2$/l or less is diluted with a further water stream to concentrations of roughly less than 3 g of $ClO_2$/l of solution.

In order that the prior art methods can be operated with satisfactory results with respect to plant safety, chlorine dioxide yield and time-specific production rate, a variety of processing variations are performed, inter alia, Use of diluted starting chemicals: respective concentrations of the chlorine dioxide solution produced falling below 26 g/l or 6 g/l.

Generating reduced pressure in the reactor by applying a vacuum: reduction of the chlorine dioxide concentration in the gas phase to <300 g/m$^3$.

Generation of reactor overpressure, e.g. by using pressure-retention valves at the reactor outlet: prevention of the formation of a gas phase by exceeding the solubility limit of chlorine dioxide; increasing the yield.

Use of batch methods having long reaction times: increasing the yield when diluted starting chemicals are used.

Use of superstoichiometric acid amounts in the chlorite/acid method and use of superstoichiometric chlorine amounts in the chlorite/chlorine method: increasing the yield.

Despite the use of these procedures, in the event of incorrect operation of the chlorine dioxide generation systems, e.g. due to loss of dilution water or by failure of pressure control, spontaneous decomposition (explosion) of chlorine dioxide can occur, or chlorine dioxide may, due to leakage or breakage of separation surfaces between the chlorine-dioxide-containing solution and the environment, lead to hazards in areas surrounding the generation systems. The use of diluted starting chemicals which leads to chlorine dioxide solutions of a concentration of less than 6 g/l, and therefore the sacrifice of relatively high time-specific generation rates of the chlorine dioxide systems, also cannot exclude hazard to the surrounding areas of the generation systems by exceeding the MAK value [maximum workplace concentration] of 0.1 ppm in the event of incorrect operation. In order to minimize these hazards, various measures are implemented at the generation systems themselves, and also at the sites where the chlorine dioxide generation systems are erected, e.g. complex servicing work on the generation systems including regular replacement of the reactors, spatially isolated erection sites for the generation systems, forced aeration and air monitoring of the atmosphere of the erection site by continuous gas analysis.

A safe method for environment and people is thus needed, with avoidance of the emission of $ClO_2$ into the environment, in particular into the chambers in which the plant is customarily operated. At the same time, the advantages resulting from the use of concentrated starting chemicals such as, e.g. reduced material transport, higher reaction rate, higher yields, lower reactor volume, should be made utilizable.

SUMMARY OF THE INVENTION

Accordingly, one object of the present invention is therefore to design the treatment of water with chlorine dioxide so as to be safer and more efficient.

An additional object of the present invention is, at a high time-specific generation rate of the chlorine dioxide methods, to minimize the hazard potential of this type of water treatment and simultaneously to reduce the expenditure on the safety installations.

These and other objects of the invention, alone or in combinations of two or more thereof, have been satisfied by the discovery of a method of treating water with chlorine dioxide ($ClO_2$), comprising:

surrounding a reaction chamber, in which the $ClO_2$ is generated, with water, wherein the water surrounding the reaction chamber is simultaneously the water to be treated; and passing a reaction solution comprising the $ClO_2$ formed in the reaction chamber out of the reaction chamber through an outlet directly into the water, thus treating the water.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The present invention relates to a method of treating water with chlorine dioxide ($ClO_2$), comprising:

surrounding a reaction chamber, in which the $ClO_2$ is generated, with water, wherein the water surrounding the reaction chamber is simultaneously the water to be treated; and passing a reaction solution comprising the $ClO_2$ formed in the reaction chamber out of the reaction chamber through an outlet directly into the water, thus treating the water.

Preferably, in the present method, the combination of the concentrations of the starting chemicals and dilution water used if desired is selected in such a manner that the concentration at the reactor outlet of the chlorine dioxide formed is greater than 3 g/l of solution, preferably greater than 26 g/l of solution, and particularly preferably greater than 80 g/l of solution.

More preferably, the reaction chamber in which the $ClO_2$ is generated is a reactor without a pressure control appliance and equipped with a free outlet and the combination of the concentrations of the starting chemicals and dilution water used if desired is selected in such a manner that the concentration at the reactor outlet of the chlorine dioxide formed is greater than 3 g/l of solution, preferably greater than 26 g/l of solution, and particularly preferably greater than 80 g/l of solution.

In a particularly preferred embodiment the reaction chamber in which the $ClO_2$ is generated is a reactor without a pressure control appliance and equipped with a free outlet, the water surrounding the reaction chamber (which is simultaneously the water to be treated) exerts a pressure on the chlorine dioxide-containing solution in the reaction chamber of a magnitude that the solubility limit of chlorine dioxide in water at a given temperature is not exceeded, and the combination of the concentrations of the starting chemicals and dilution water used if desired is selected in such a manner that the concentration at the reactor outlet of the chlorine dioxide formed is greater than 3 g/l of solution, preferably greater than 26 g/l of solution, and particularly preferably greater than 80 g/l of solution.

The method of the present invention enables safe working by avoiding the escape of $ClO_2$ into working rooms or the surrounding areas and eliminates adverse consequences of explosive decompositions. The reaction chamber in which the $ClO_2$ is generated is completely surrounded by water and the water which surrounds the reaction chamber is simultaneously the water which is to be treated.

Shifting the point of formation of the chlorine dioxide out of spaces accessed by people and the storage site of starting chemicals significantly increases safety. Leaks up to explosions of the reaction chamber are virtually neutralized by the large volume of water.

The resultant $ClO_2$ is passed directly without bypasses from the reaction chamber in which the $ClO_2$ is formed into the water which is to be treated, since the outlet is directly on the end of the reaction chamber and is therefore likewise surrounded by the water which is to be treated.

It has likewise surprisingly been found that the combination of the use of concentrated starting chemicals with dilution water used, if desired, which leads to a chlorine dioxide concentration in the reaction chamber of greater than 26 g/l of solution and particularly preferably greater than 80 g/l, no autodecomposition of chlorine dioxide occurs if the mean residence time in the reaction chamber is within a certain time range which prevents the formation of gaseous chlorine dioxide and the chlorine dioxide solution leaving the reaction chamber is abruptly diluted to concentrations in the milligram range. In addition, it has been found that the necessary superstoichiometric, yield-increasing increased amounts of acid or chlorine can be reduced by increasing the chlorine dioxide concentration in the reaction chamber.

The advantages of the present invention method will be described in more detail below.

A leak of the reaction chamber, in particular of the reactor, can be simply and safely handled in the water which is continuously flowing past its wall. The chlorine dioxide, in particular, which escapes in the event of a leak of the reaction chamber is diluted to a non-critical concentration and transported away. The same applies to the starting chemicals (reactants) which possibly exit from the reaction chamber, in particular the reactor. Since the synthesis of chlorine dioxide from concentrated starting chemicals can proceed without dilution by water, the necessary superstoichiometric, yield-increasing increased amounts of acid or chlorine can be reduced and there is in addition a significant increase of the reaction rate, resulting from a high specific generation rate of the reaction chamber. By reducing the necessary median residence time of the reactants in the reaction chamber, there is the possibility of minimizing the reaction chamber volume, as a result of which, e.g. the installation of the reaction chamber, in particular the reactor, into a pipe becomes possible, through which pipe the water which is to be treated flows. In addition, from the safety aspect, there is an improvement of the ratio between the amount of chlorine dioxide permanently present in the reaction chamber during synthesis and the amount of water which is to be treated.

The shifting of the point of production of the chlorine dioxide out of the spaces accessed by people and the storage site of the starting chemicals significantly increases safety.

Reaction chamber leaks up to reaction chamber explosions are virtually neutralized by the large amount of water which is to be treated relative to the amount of chlorine dioxide which is present in the reaction chamber.

The features of the present method enable safe working, even with the use of concentrated starting chemicals without dilution water, by avoiding the escape of $ClO_2$ into working rooms or the surroundings and eliminates adverse consequences of explosive decompositions.

The use of one reactor as reaction chamber is preferred.

According to the present method, the resultant $ClO_2$ is passed directly into the water which is to be treated without bypasses or further additional lines directly from the reaction chamber in which the $ClO_2$ is formed, since the outlet is situated directly at the end of the reaction chamber, preferably the reactor, and is therefore likewise surrounded by the water which is to be treated. This measure is a preferred embodiment of the method.

In addition, there is the possibility of transporting the chlorine dioxide solution exiting from the reaction chamber via an offtake line situated at the end of the reaction chamber (outlet) to one or more other sites. This can be used, inter alia, for distribution of the chlorine dioxide solution in a large total system to be treated or for apportionment over a plurality of individual systems to be treated. In such a system, a preferred embodiment of the present invention is a method of treating water with chlorine dioxide ($ClO_2$), comprising:

surrounding a reaction chamber, in which the $ClO_2$ is generated, with water; and passing a reaction solution comprising the $ClO_2$ formed in the reaction chamber out of the reaction chamber through an offtake situated at one end of the reaction chamber to one or more other sites, directly into the water at the one or more other sites, thus treating the water.

For the offtake, all appliances are suitable by which the above described effects can be achieved, such as, for example, fixed mounted lines or flexible tube systems. At the end of the offtake, units for distributing the chlorine dioxide solution, e.g. water-jet liquid pump, circulation pump, can also be placed.

The expression, passed into the water which is to be treated, means that the $ClO_2$ from the reaction chamber is introduced into the water which is to be treated more preferably by the starting chemicals introduced directly via an offtake into the reaction chamber and if desired by the dilution water directly or via an offtake introduced into the reaction chamber.

The renewal rate at the outlet of the reaction chamber, preferably the reactor outlet, or the offtake, of the water which is to be treated can be increased by technical appliances.

The reaction chamber, preferably the reactor, is preferably operated without a pressure control appliance. A free outlet at the end of the reaction chamber, preferably the reactor outlet, or the offtake, ensures that the pressure in the reaction chamber can only increase up to the value which is exerted on the reaction chamber by the surrounding water.

The concentration of the chlorine dioxide which forms in the reaction chamber, preferably the reactor can be set in combination with pressure and temperature of the surrounding water in such a manner that the solubility limit of chlorine dioxide in water is not exceeded. As a result, the formation of a 2-phase system due to a chlorine dioxide gas phase which forms can be prevented.

The pressure which is exerted on the reaction chamber by the water which is to be treated can be altered, for example, by the immersion depth of the reaction chamber, preferably the reactor, in a water reservoir. The pressure conditions for a reactor which is used in a pipe can be influenced, for example, by shut-off elements integrated into the pipe.

If the water which is to be treated is renewed at the outlet of the reaction chamber, preferably the reactor, at an appropriate rate, the concentration of the chlorine dioxide solution leaving the reaction chamber, preferably the reactor, can be abruptly shifted to a milligram range. This can be achieved, for example, by the reaction chamber, preferably the reactor, being used in a pipe through which water to be treated flows at a rate which corresponds to the desired renewal rate.

A reaction chamber, preferably a reactor, immersed in a water reservoir can be placed locally in the vicinity of the suction side of a circulation pump in order to ensure the corresponding renewal rate at the end of the reaction chamber, preferably the reactor outlet, or the offtake, of the water to be treated. If a circulation pump is not present, a variety of conventional alternatives are available, such as, for example, water-jet liquid pumps or other circulation appliances, which induce the desired renewal rate at the end of the reaction chamber, preferably the reactor outlet or the offtake, of the water which is to be treated.

In principle, all chemical production methods of $ClO_2$ can be employed in the reaction chamber, in particular the methods 1. to 3. which are described in the background section above, or else starting from chlorate.

Preference in this invention is given to the hydrochloric acid-chlorite method (1.). In this method the starting chemicals (reactants) of alkali metal chlorite salt, preferably sodium chlorite, can be present in aqueous solutions of from 3.5% to 40%. The acid is preferably hydrochloric acid in a concentration of 3.5% to 42%.

In a particularly preferred embodiment of the invention, concentrated starting chemicals are used and the hydrochloric acid-chlorite method (1) is employed. The concentration of hydrochloric acid is then about 33-42% and that of the sodium chlorite solution is about 25-40%. The starting chemicals are not diluted before or in the reaction chamber, preferably the reactor.

The starting chemicals (reactants), in particular acid and chlorite, are passed into the reaction chamber as aqueous solution, as described above, separately by inherent pressure of the solutions or using pumps, and brought to reaction.

In a preferred embodiment, the reactants are used as concentrated solutions, and the use of dilution water is dispensed with, so that the chlorine dioxide concentration at the end of the reactor chamber, preferably at the end of the reaction chamber, preferably at the reactor outlet or the offtake, is set to greater than 80 g/l of solution. Alternatively, dilution water can be used in order to set the chlorine dioxide concentration at the end of the reaction chamber, preferably at the reactor outlet or the offtake, between greater than 3 g/l of solution, preferably greater than 26 g/l of solution, and particularly preferably greater than 80 g/l of solution.

The device for carrying out the method according to the invention is not particularly limited, so long as it has the requisite ability to have the reaction chamber surrounded by the water to be treated and has an outlet through which the produced chlorine dioxide can be passed into the water to be treated. The device comprises essentially any suitable devices and apparatuses. The device typically includes one or more tanks for the starting chemicals (reactants), such as, in a preferred embodiment, an acid storage tank and a chlorite storage tank, an aqueous acid solution being stored in the acid storage tank and a solution of an alkali metal salt of a chlorite ion being stored in the chlorite storage tank. Apparatuses are provided which not only can feed the suitable components into the storage tanks but also can take off solutions. Preferably, these apparatuses include pumps and feed lines which are sufficient to ensure the flow rates of the starting chemicals (reactants), in a preferred embodiment, aqueous acid solutions and solutions of alkali metal salts of a chlorite ion, and also of the amount of dilution water. Those of ordinary skill in the art can readily determine suitable sizes for the relevant storage tanks, feed lines and pumps in order to achieve the required feed rates of reactant solutions (e.g. aqueous acid solutions, solutions of an alkali metal salt of a chlorite ion).

Preferably, the device has embodiments having at least two pumps for two starting chemicals (reactants), but in a preferred embodiment, one for the solution of the alkali metal salt of a chlorite ion and the other for the aqueous acid solution, or three pumps, if dilution water is added.

The device further comprises an apparatus for mixing the solution of the starting chemicals (reactants), in a preferred embodiment the solution which contains the alkali metal salt of a chlorite ion and the aqueous acid solution, in order to provide an aqueous reaction solution of the starting chemicals (reactants). Any apparatus which mixes the abovementioned solutions adequately can be used, including conventional T-pieces or other connection elements which combine two streams or three streams to form one combined throttle lines and/or a stirred tank. The aqueous reaction solution can then be fed into the reaction chamber after mixing. Preferably, the two reactants and the dilution water which is used if desired are mixed in the reaction chamber. The mixing process can be introduced by any appliance such as baffle plates, injectors or packings, for example, which ensures optimum mixing.

The reaction chamber which is used can be any reactor which is able to initiate the reaction between the starting chemicals (reactants), in a preferred embodiment the aqueous acid solution and the alkali metal salt of a chlorite ion, including continuous stirred reactors, simple tanks, mass-flow or plug-flow reactors and tubular reactors. A tubular reactor is particularly preferred. Usually, a chlorine dioxide generation unit comprises only one tubular reactor, but the generation rate of a unit can be increased by the parallel arrangement of a plurality of reactors, for example to form a tube bundle. The reactor can be not only temperature-controlled, but also comprise a good heat-conducting material in order to release liberated heat of reaction to the surrounding water. The material of which the reactor is fabricated comprises materials which exhibit good stability to the respective reaction solutions. In the generation of chlorine dioxide solutions having concentrations greater than 28 g/l, the reaction material used is, for example, titanium, alloy 31, glass or chemistry materials e.g. polymers such as e.g. PVDF or PTFE. The $ClO_2$ is removed from the reactor by any mechanism which is able to remove an aqueous solution from a reactor. Preferably, the reaction is carried out continuously and $ClO_2$ is removed continuously from the reactor. After the $ClO_2$ leaves the reactor, it is metered directly into the water which is to be treated, or transported to one or more other sites via an offtake situated at the reactor outlet.

A tubular reactor is preferably used according to the present invention. Generally, the tube of the tubular reactor is constructed in such a manner that it has a sufficient length to ensure sufficient residence time in the reactor in order, with respect to flow rate of the reaction solution, its concentration of reactants and the temperature of the reaction solution, to react the components sufficiently. A particularly preferred reactor which can be used for producing a suitable generator of aqueous chlorine dioxide on site is a (temperature-controlled) tubular reactor which contains one or more tube coils. Those of ordinary skill in the art are able to vary the size and shape of the reactor as a function of the amount of aqueous chlorine dioxide to be produced, the flow rate and concentration of the reactants, the pH of the aqueous reaction solution, the pH of the $ClO_2$ and the temperature of the reactor. Those of ordinary skill in the art are likewise able to modify the temperature of the reactor appropriately.

The reaction time in the reaction chamber can vary. With increasing concentration of the reactants in the reaction chamber, the optimum of the residence time decreases. If a solution having a chlorine dioxide concentration of 20 g/l is produced, the median reactor residence time is from about 4 minutes to 60 minutes, preferably from approximately 4 to 6 minutes, in order to achieve a yield of approximately 85%. If the chlorine dioxide concentration according to the particularly preferred embodiment increases to greater than 80 g/l, the median reactor residence time is from about 0.1 minutes to 1.5 minutes, preferably from 0.3 to 0.6 minutes, particularly preferably approximately 0.4 minutes for a 95% yield. The minimum of the median residence time can be achieved when the reactants are used as concentrated solutions, dilution water is not used and the necessary stoichiometric excess of acid or chlorine is minimized.

The conductivity value is preferably measured in the solution leaving the reaction chamber before it is released to the water which is to be treated. For example, an inductive measuring method can be used. From the conductivity values measured, information can be obtained with respect to the chemical reaction of the reactants used and also if desired with respect to the amount of dilution water used.

The chlorine dioxide solution leaving the reactor outlet, or the offtake, is diluted in such a manner that the renewal rate at the reactor outlet of the water which is to be treated is from about 0.1 $m^3$/h to 20 $m^3$/h per gram and hour of generated chlorine dioxide, preferably from 1 $m^3$/h to 4 $m^3$/h per gram and hour of generated chlorine dioxide.

Figure 1:
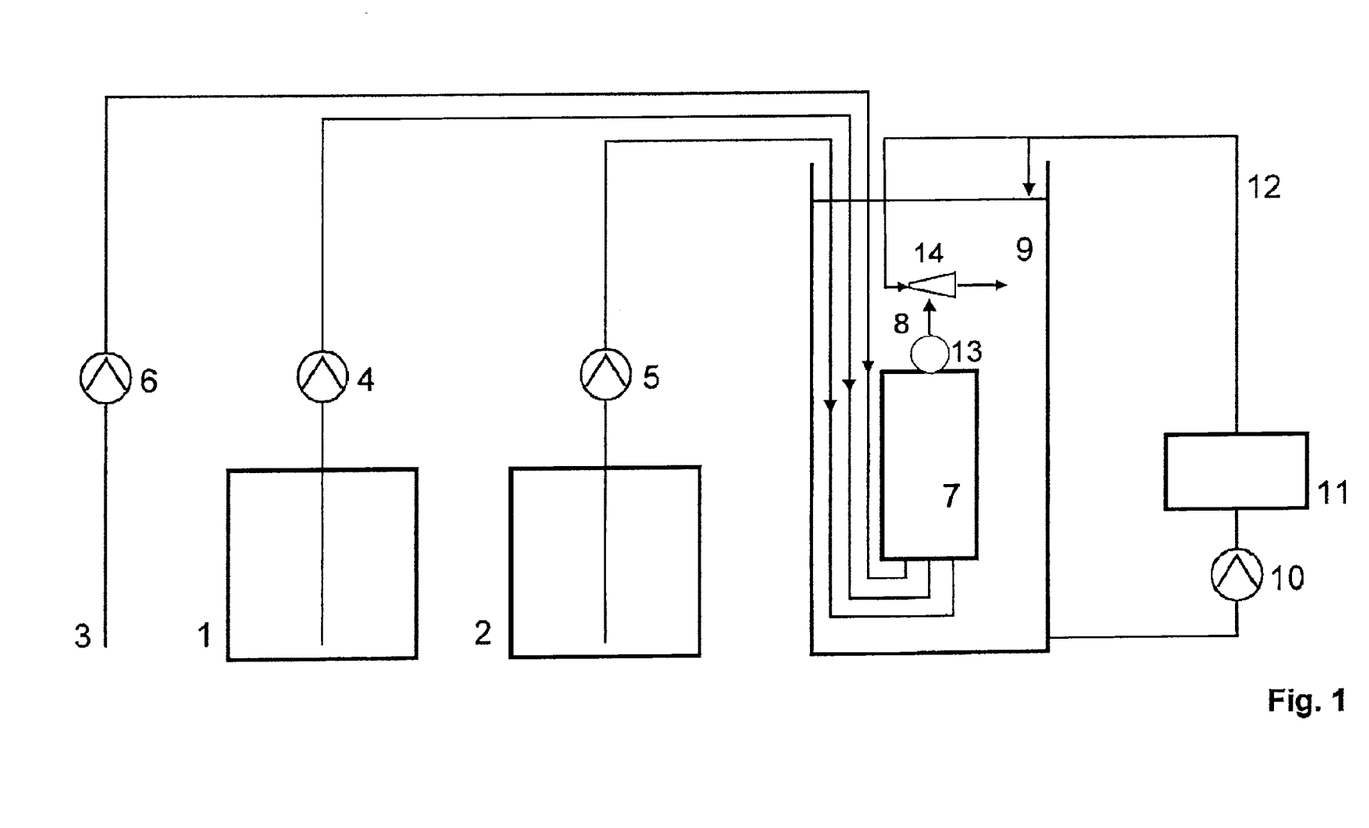
FIG. 1 shows an outline structure of an embodiment of a device for carrying out the method according to the invention, without being restricted to defined starting chemicals (reactants).
Figure 2:
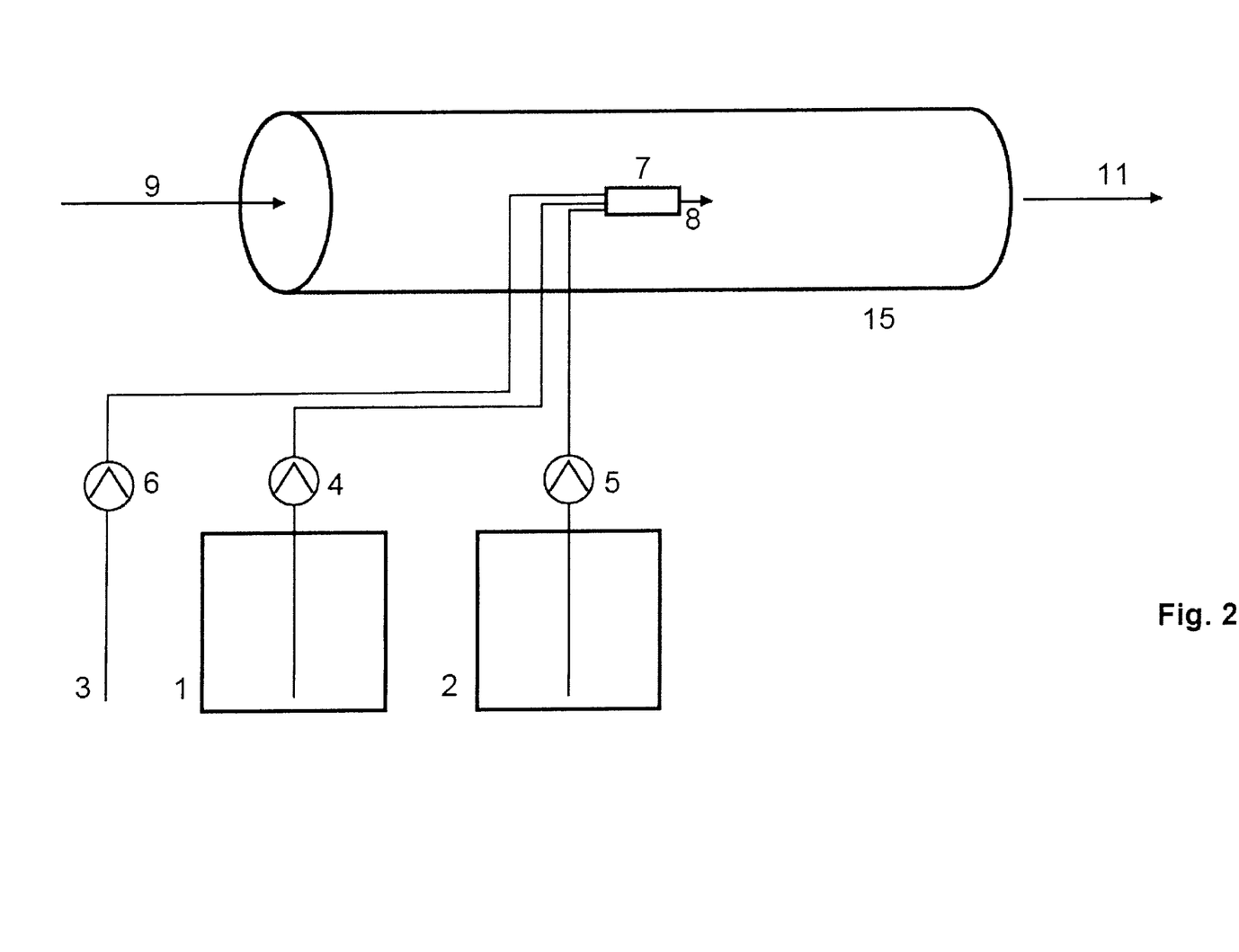
FIG. 2 shows an outline structure of a further preferred device for carrying out the present invention method.

The method according to the invention can be carried out, for example, by use of the devices pictured in FIG. 1 and FIG. 2.

FIG. 1 shows an outline structure for carrying out the method according to the invention, without being restricted to defined starting chemicals (reactants). The units having the specified number are therefore to be employed correspondingly generally in their function for all methods having the various possible starting chemicals (reactants) and can readily be recognized by those skilled in the art.

In FIG. 1, the device for treating water with chlorine dioxide comprises two tanks for the starting chemicals (reactants), in particular a chlorite storage tank 1 having a transport pump 4 and an acid storage tank 2 having a transport pump 5. The water pump 6 is supplied via the water connection 3. All three transport pumps are connected via an individual line to the bottom side of the reactor 7. In the reactor are situated conventional appliances which ensure rapid complete mixing of the supplied components in the reaction chamber. By variation of the concentration contents of the reactant solutions or of the amount of dilution water used, the concentration of the resultant chlorine dioxide solution is set to greater than 3 g/l, preferably greater than 26 g/l, and particularly preferably to greater than 80 g/l.

At the top (in the Figure), opposite, end of the reactor 7 there is situated the reactor outlet 8, upstream of which is connected a conductivity measurement 13.

At the transfer of the chlorine dioxide solution into the water which is to be treated, a water-jet liquid pump 14 can be arranged, as a result of which the renewal rate of the water which is to be treated at the chlorine dioxide inlet can be increased. The feed line from the reactor outlet 8 to the water-jet liquid pump 14, in this case, has a relief bore hole which ensures that the pressure of the water which is to be treated 9 acts in the reactor 7.

The reactor is completely surrounded by the water which is to be treated 9 which flows through an intermediate store. The treated water is taken off from the intermediate store by a suction line and fed by the circulation pump 10 to the site of use—treated water—11. Via a return line 12, then water which is again to be treated 9 is recycled to the intermediate store and again passes through the reaction outlet 8 or the outflow from the water-jet liquid pump 14. The reactor outlet 8 can also be placed close in position to the suction side of the circulation pump 10 in order to ensure rapid exchange of the water to be treated 9 at the reactor outlet 8. By suitable choice of the parameters "depth of immersion of reactor in the water to be treated" (pressure) and "concentration of the chlorine dioxide solution generated in the reactor", taking into account the temperature of the water which is to be treated, as shown by way of example in FIG. 3, the formation of a chlorine dioxide gas phase can be prevented. In addition there is the possibility of transporting the chlorine dioxide solution exiting from the reactor 7 via an offtake (which is not shown in FIG. 1) situated at the reactor outlet 8 to one or more other sites. There, units for distributing the chlorine dioxide solution, e.g. water-jet liquid pump, circulation pump, can also be placed.

FIG. 2 shows an outline structure for carrying out the method according to the invention, without being restricted to defined starting chemicals (reactants). The units having the specified number are therefore to be employed in their function correspondingly generally for all methods having the various possible starting chemicals (reactants) and may be readily recognized by those skilled in the art.

A further preferred device for the method according to the invention is shown in FIG. 2. In this case, it is essential to the invention that the reaction chamber is situated in a pipe 15, the water which is to be treated flowing through the pipe and the water which is to be treated flowing around the reaction chamber.

In FIG. 2, the reactor 7 is connected identically as in FIG. 1 to the same feed lines. The reactor 7 is likewise surrounded by the water which is to be treated 9, but the reactor 7 is situated in a pipe 14 through which water to be treated 9 flows, which pipe feeds the water which is to be treated 9, after it passes through the reactor outlet 8, to the site of use—treated water—11.

Figure 3:
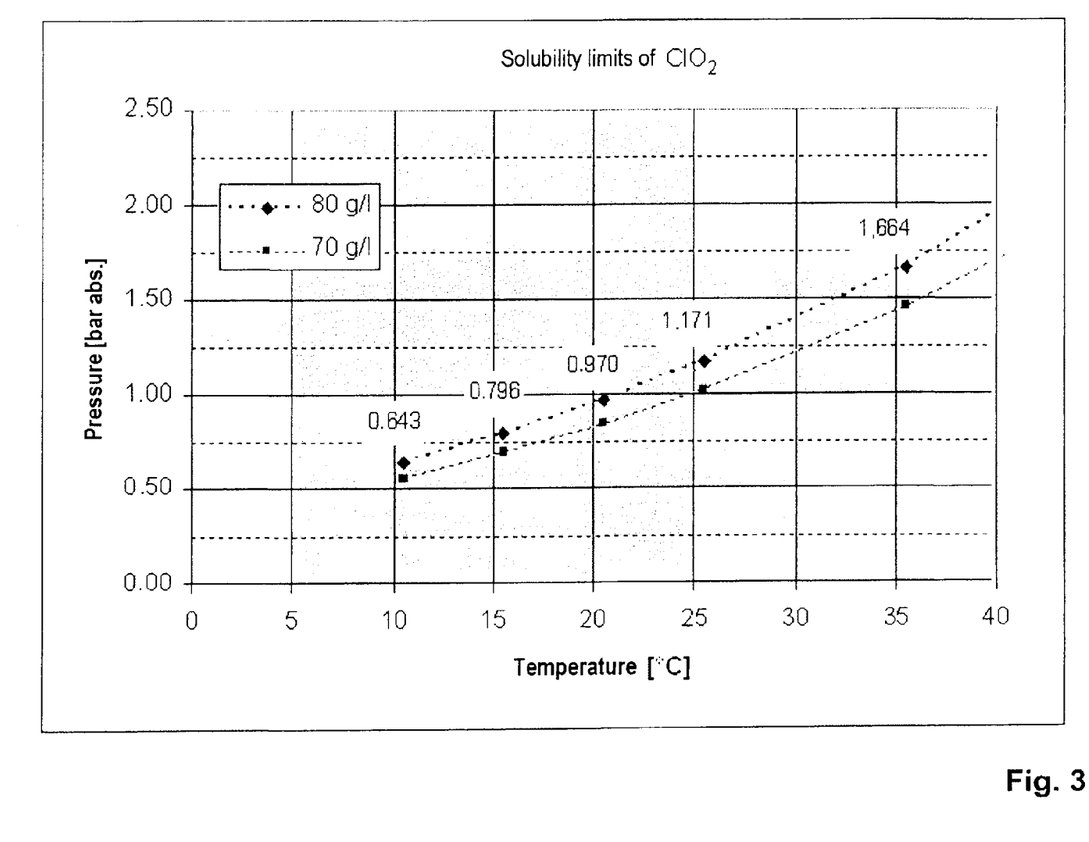
FIG. 3 shows the solubility limits of chlorine dioxide in an aqueous solution as a function of pressure and temperature for the example of chlorine dioxide concentrations of 70 g/l and 80 g/l.

In FIG. 2, the reactor 7, as in FIG. 1, can likewise be supplied with dilution water, but a preferred variant is to allow the reactor 7 to react without dilution of the reactants by water (dilution water transport pump 6 shut off) in the reaction chamber. In this case the concentration of the resultant solution at the reactor outlet 8 can be greater than 9 g/l [without dilution water the $ClO_2$ content increases to 9.1 g/l, even when 3.5% strength reactants are used], preferably greater than 26 g/l, and particularly preferably to greater than 80 g/l, of chlorine dioxide per liter. In this preferred variant, it is advantageous to reduce the size of the reactor volume as much as possible. Generally, no further appliances are necessary for increasing the renewal rate at the reactor outlet 8 of the water which is to be treated 9 in order to shift the concentration of the chlorine dioxide solution after entry into the water which is to be treated 9 rapidly from preferably greater than 80 g per liter into the milligram range. Likewise, it is generally not difficult to set the pressure of the water which is to be treated 9 in the pipe 14 in such a manner that the solubility limit of the chlorine dioxide is not exceeded in the aqueous solution in the reactor 7, as shown in FIG. 3.

EXAMPLES

The method according to the invention is illustrated by the following examples, without being restricted thereto:

Example 1

The device described in FIG. 1 is used. The aqueous solution in the chlorite storage tank 1 contains 25% sodium chlorite and 2.5 l/h of this solution are passed by the transport pump 4 into the reactor 7. From the acid storage tank 2, 2.5 l/h of a 32% strength aqueous hydrochloric acid solution are simultaneously fed to the reactor 7 by the transport pump 5. Via the dilution water rate of 5 l/h, which is likewise simultaneously fed to the reactor 7 from the water connection 3 by the transport pump 6, the concentration of the resultant chlorine dioxide solution is set to 42 g/l [at a yield of 92%]. The reactor has a free volume of 0.33 liters and the residence time of the reaction mixture in the reaction chamber is 2 minutes. 10 liters of chlorine dioxide solution having a content of 42 g/l are fed per hour via the reactor outlet 8 to a water-jet liquid pump 14 which is operated with the water which is to be treated and subsequently mixed with the returned amount of water which is to be treated. The value determined by the conductivity measurement 13 is 0.42 S/cm. 1000 $m^3$ of the water enriched with chlorine dioxide are taken off from the intermediate store by the circulation pump—treated water—10 and provided to the site of use—treated water—11. Via the return—water to be treated—12, the water which is depleted in chlorine dioxide is returned to the intermediate store. On the way to the intake point of the circulation pump—treated water—10, the water which is to be treated takes up the exiting chlorine dioxide-containing water and rapidly reduces the chlorine dioxide concentration in the mixed water to 0.42 mg/l in this process. The reactor outlet 8 is lowered 4 meters below the water surface in the intermediate store and the temperature of the water which is to be treated is 32° C. In the devices described in Example 1, the water which is to be treated 9 is recirculation cooling water of a circulation cooling stage which is situated in a cooling tower pond (intermediate store). By means of the circulation pump 10, the cooling water is passed over heat-exchange surfaces of a chemical production plant having exothermic heat sources (site of use—treated water—11) and subsequently trickled over the internals of an evaporative cooling tower before it again reaches the cooling tower pond (intermediate store). The cooling tower pond has a volume of 800 $m^3$. The water level in the intermediate store is under level control, in such a manner that the evaporated cooling water is automatically replaced by fresh water.

Example 2

The device described in FIG. 2 is used. The aqueous solution in the chlorite storage tank 1 contains 25% sodium chloride and 6 l/h of this solution are passed into the reactor 7 by the transport pump 4. From the acid storage tank 2, 5 l/h of a 30% strength aqueous hydrochloric acid solution are simultaneously fed to the reactor 7 by the transport pump 5. The reactor 7 is built into a pipe 14 through which an amount of 100 $m^3$ of water to be treated 9 flows per hour. No dilution water is fed to the reactor via transport pump 6. The reactor has a free volume of 0.075 liters and the residence time of the reaction mixture in the reaction chamber is 0.4 minutes. 11 liters of chlorine dioxide solution having a content of 94 g/l are delivered per hour via the reactor outlet 8 into the water which is to be treated 9 flowing around the reactor 7, as a result of which the concentration of the reaction mixture at the reactor outlet 8 is abruptly reduced to 10 mg/l by mixture with the water which is to be treated 9. At an acid excess of 300%, the chlorine dioxide is generated at a yield of 95%. The pressure of the water to be treated 9 in the pipe 14 is 5.5 bar and its renewal rate at the reactor outlet 8 is 0.1 m$^3$/h per gram and hour of generated chlorine dioxide. The treated water 11 is provided to the site of use at the end of the pipe. The appliances described in Example 2 are the treatment of 100 m$^3$/h of washwater which is used with a chlorine dioxide concentration of 10 mg/l in a cleaning system.

Example 3

The device described in FIG. 1 is used. The aqueous solution in the chlorite storage tank 1 contains 24.5% sodium chlorite and 5 l/h of this solution are passed into the reactor 7 by the transport pump 4. From the acid storage tank 2, 5 l/h of a 32% strength aqueous hydrochloric acid solution are simultaneously fed to the reactor 7 by the transport pump 5. Via the dilution water rate of 28 l/h which is likewise simultaneously fed to the reactor 7 from the water connection 3 by the transport pump 6, the concentration of the resultant chlorine dioxide solution is set to 19.7 g/l [at a yield of 83%]. The reactor has a free volume of 6 liters and the residence time of the reaction mixture in the reaction chamber is 9.5 minutes. 38 liters of chlorine dioxide solution having a content of 19.7 g/l are delivered via the reactor outlet 8, which is situated in the vicinity of the suction line of the circulation pump 10, into the water to be treated 9 which surrounds the reactor. 2000 m$^3$ of the water enriched with chlorine dioxide are taken off per hour from the intermediate store by the circulation pump—treated water—10 and provided to the site of use—treated water—11. Via the return—water to be treated—12, the water which is depleted in chlorine dioxide passes back into the intermediate store. On the way to the suction point of the circulation pump—treated water—10, the water takes up the chlorine-dioxide-containing water exiting from the reactor outlet 8 and in this process rapidly reduces the chlorine dioxide concentration in the mixed water below the critical concentration of 6 g/l. Upstream of the site of use—treated water—11, the concentration of chlorine dioxide is about 0.4 mg per liter of water.

The present application is based on German Patent Applications DE102007061360.3, filed Dec. 19, 2007; DE102008041081.0, filed Aug. 7, 2008; and DE102008042424.2, filed Sep. 29, 2008, the entire contents of each of which are hereby incorporated by reference.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of treating an aqueous stream with chlorine dioxide (ClO$_2$), comprising:
   generating a chlorine dioxide in a reaction chamber surrounded by the aqueous stream to be treated, and
   passing the chlorine dioxide from the reaction chamber to the surrounding aqueous stream to be treated,
   wherein
   the reactor reaction chamber has a free outlet in contact with the surrounding aqueous stream, and the minimum pressure in the reaction chamber is the pressure generated by the surrounding aqueous stream,
   the surrounding aqueous stream to be treated exerts a pressure on the chlorine dioxide in the reaction chamber of a magnitude that the formation of a chlorine dioxide gas phase in the reaction chamber is prevented, and
   the reaction chamber is operated without additional applied pressure control to prevent chlorine dioxide gas phase formation in the reaction chamber.

2. The method according to claim 1, wherein the reaction chamber is a reactor.

3. The method according to claim 2, wherein the reactor is a tubular reactor.

4. The method according to claim 1, wherein reactants used to generate the chlorine dioxide, and optionally dilution water, are mixed in the reaction chamber.

5. The method according to claim 1, wherein the reaction time for the generation of the chlorine dioxide in the reaction chamber is from 4 to 60 minutes.

6. The method according to claim 5, wherein the reaction time is from 4 to 6 minutes.

7. The method according to claim 1, wherein the reaction time is from 0.1 to 1.5 minutes.

8. The method according to claim 7, wherein the reaction time is from 0.3 minutes to 0.6 minutes.

9. The method according to claim 1, wherein the chlorine dioxide is generated from an alkali metal chlorite salt and hydrochloric acid as reactants.

10. The method according to claim 1, wherein the chlorine dioxide is generated from sodium chlorite and hydrochloric acid as reactants.

11. The method according to claim 10, wherein the concentration of the hydrochloric acid is 33-42% and that of the sodium chlorite solution is 25-40%.

12. The method according to claim 1, wherein the chlorine dioxide is generated from sodium chlorite in an aqueous solution of from 3.5% to 40%.

13. The method according to claim 1, wherein the chlorine dioxide is generated from hydrochloric acid in a concentration of from 3.5% to 42%.

14. The method according to claim 1, wherein the chlorine dioxide is generated from sodium chlorite and chlorine as reactants.

15. The method according to claim 1, wherein dilution water is used in the generation of the chlorine dioxide.

16. The method according to claim 1, wherein a conductivity value of the reaction solution is measured in the reaction solution leaving the reaction chamber.

17. The method according to claim 1, wherein no dilution water is used in the generation of the chlorine dioxide.

18. The method according to claim 1, wherein concentrations of reactants used in generating chlorine dioxide are selected in such a manner that a concentration of chlorine dioxide at the end of the reaction chamber outlet is greater than 3 g/l of solution.

19. The method according to claim 18, wherein concentrations of reactants used in generating chlorine dioxide are selected in such a manner that a concentration of chlorine dioxide at the end of the reaction chamber outlet is greater than 26 g/l of solution.

20. The method according to claim 19, wherein concentrations of reactants used in generating chlorine dioxide are selected in such a manner that a concentration of chlorine dioxide at the end of the reaction chamber outlet is greater than 80 g/l of solution.

21. A method according to claim 1, wherein the water of the surrounding aqueous stream which is to be treated is recirculation cooling water.

22. The method according to claim 1, wherein the reaction chamber has a free outlet in direct contact with the surrounding aqueous stream.

23. The method according to claim 1, wherein the reaction is carried out continuously and chlorine dioxide is removed continuously from the reaction chamber.

24. A method of treating an aqueous stream with chlorine dioxide ($ClO_2$), comprising:
- generating an aqueous chlorine dioxide containing reaction solution in a reaction chamber surrounded by the aqueous stream to be treated, and
- passing the chlorine dioxide containing reaction solution from the reaction chamber to the surrounding aqueous stream to be treated, wherein

- the reaction chamber has a free outlet in contact with the surrounding aqueous stream,
- the surrounding aqueous stream to be treated exerts a pressure on the chlorine dioxide in the aqueous chlorine dioxide reaction solution in the reaction chamber of a magnitude that the solubility limit of chlorine dioxide in water at a given temperature in the reaction chamber is not exceeded, and
- the reaction chamber is operated without additional applied pressure control to prevent chlorine dioxide gas phase formation in the reaction chamber.

25. The method according to claim 24, wherein the reaction chamber has a free outlet in direct contact with the surrounding aqueous stream.

26. The method according to claim 24, wherein the reaction is carried out continuously and chlorine dioxide is removed continuously from the reaction chamber.

\* \* \* \* \*